United States Patent
Leleti et al.

(10) Patent No.: US 11,279,668 B2
(45) Date of Patent: Mar. 22, 2022

(54) ASYMMETRIC SYNTHESIS OF ALPHA-(DIARYLMETHYL) ALKYL AMINES

(71) Applicant: PIRAMAL PHARMA LIMITED, Mumbai (IN)

(72) Inventors: Rajender Reddy Leleti, Gujarat (IN); Sharadsrikar Kotturi, Gujarat (IN); Yogesh Waman, Gujarat (IN); Chirag Patel, Gujarat (IN); Rajesh Shenoy, Gujarat (IN)

(73) Assignee: PIRAMAL PHARMA LIMITED, Mumbai (IN)

( * ) Notice: Subject to any disclaimer, the term of this patent is extended or adjusted under 35 U.S.C. 154(b) by 20 days.

(21) Appl. No.: 16/981,356

(22) PCT Filed: Mar. 20, 2019

(86) PCT No.: PCT/IB2019/052247
§ 371 (c)(1),
(2) Date: Sep. 16, 2020

(87) PCT Pub. No.: WO2019/180627
PCT Pub. Date: Sep. 26, 2019

(65) Prior Publication Data
US 2021/0061752 A1  Mar. 4, 2021

(30) Foreign Application Priority Data

Mar. 21, 2018  (IN) .............. 201821010383

(51) Int. Cl.
| | | |
|---|---|---|
| C07C 209/62 | (2006.01) | |
| C07C 313/06 | (2006.01) | |
| C07D 307/52 | (2006.01) | |
| C07C 211/27 | (2006.01) | |

(52) U.S. Cl.
CPC .......... *C07C 209/62* (2013.01); *C07C 313/06* (2013.01); *C07D 307/52* (2013.01); *C07C 211/27* (2013.01)

(58) Field of Classification Search
None
See application file for complete search history.

(56) References Cited

U.S. PATENT DOCUMENTS

2014/0171639 A1 * 6/2014 Biswas ................... A61P 11/00
544/91

FOREIGN PATENT DOCUMENTS

| WO | 2007/104162 | 9/2007 |
| WO | 2008/136756 | 11/2008 |
| WO | 2015/002915 | 1/2015 |

OTHER PUBLICATIONS

ISR for International Application PCT/IB2019/052247, (dated 2019).
Written Opinion for International Application PCT/IB2019/052247, (dated 2019).
Derek A. Coganet, et al., "Asymmetric Synthesis of Chiral Amines by Highly Diastereoselective 1,2-Additions of Organometallic Reagents to N-tert-Butanesulfinyl Imines", Tetrahedron, (1999), vol. 55, No. 29, pp. 8883-8904, XP004171393 [A] 1-8 * scheme 2; tables 1 and 2 * DOI: http://dx.doi.org/10.1016/S0040-4020(99)00451-2, (1999).
Jonathan A. Ellman et al., "N-tert-Butanesulfinyl Imines: Versatile Intermediates for the Asymmetric Synthesis of Amines", Accounts of Chemical Research, (2002), vol. 35, No. 11, pp. 984-995, XP055638450 [A] 1-8 * Figures 2, 3 and 5; and table 1 * DOI: http://dx.doi.org/10.1021/ar020066u, (2002).
Mary Ann T. Robak, et al., "Synthesis and Applications of tert-Butanesulfinamide", Chemical Reviews, (2010), vol. 110, No. 6, pp. 3600-3740, XP055638453 [A] 1-8 * scheme 2; and tables 1 and 2 * DOI: http://dx.doi.org/10.1021/cr900382t, (2010).
Leleti Rajender Reddy et al., "Asymmetric Synthesis of a-(Diarylmethyl) Alkyl Amines through Regioselective Lithiation of a-Diarylmethanes and the Diastereoselective Addition to Ellman's Imines", Journal of Organic Chemistry, (2018), vol. 83, No. 12, pp. 6573-6579, XP055638456 [PX] 1-8 * abstract; schemes 1-5; and tables 1 and 2 * DOI: http://dx.doi.org/10.1021/acs.joc.8b00879, (2018).
Arava Amaranadha Reddy, et al., "Addition of the Lithium Anion of Diphenylmethanol Methyl/Methoxymethyl Ether to Nonracemic Sulfinimines: Two-Step Asymmetric Synthesis of Diphenylprolinol Methyl Ether and Chiral (Diphenylmethoxymethyl) amines", Journal of Organic Chemistry, (2018), vol. 83, No. 18, pp. 10776-10785, XP055638457 [PA] 1-8 * abstract; and chart 1 * DOI: http://dx.doi.org/10.1021/acs.joc.8b01381, (2018).

* cited by examiner

*Primary Examiner* — Sudhakar Katakam
*Assistant Examiner* — Jennifer C Sawyer
(74) *Attorney, Agent, or Firm* — Ladas & Parry LLP

(57) ABSTRACT

The present invention relates to an improved asymmetric synthesis of alpha-(diarylmethyl) alkyl amines (hereafter referred to as the compound (1)) or its pharmaceutically acceptable salt and derivatives. The process comprises an unusual substrate specific regioselective lithiation of alpha-diarylmethanes. followed by its highly diastereoselective addition to N-tert-butanesulfinylimines resulting in the selective formation of chiral alpha-(diarylmethyl) alkyl amines 4 and chiral amine 5; which on subsequently removing the sulfinyl group provides corresponding alpha-(diarylmethyl) alkyl amines (1) or relative chiral amines (1").

4 Claims, No Drawings

US 11,279,668 B2

ASYMMETRIC SYNTHESIS OF ALPHA-(DIARYLMETHYL) ALKYL AMINES

FIELD OF THE INVENTION

The present invention relates to an improved asymmetric synthesis of alpha-(diarylmethyl) alkyl amines (hereafter referred to as the compound (1)) or relative chiral amines (1") or its pharmaceutically acceptable salt and derivatives.

BACKGROUND OF THE INVENTION

The following discussion of the prior art is intended to present the invention in an appropriate technical context, and allows its significance to be properly appreciated. Unless clearly indicated to the contrary, reference to any prior art in this specification should not be construed as an expressed or implied admission that such art is widely known or forms part of common general knowledge in the field.

The compounds of formula (1), alpha-(diarylmethyl) alkyl amines are ubiquitous structural motifs present in many drugs, drug candidates as well as bioactive substances; such as Denagliptin, Melanocortin-5 receptor (MC5R) active substance, HIV Protease Inhibitor active compounds and so on. The compounds of formula (1) are also effectively used in asymmetric synthesis of chiral polydentate ligands. The compounds of formula (1), alpha-(diarylmethyl) alkyl amines are structurally represented as follows;

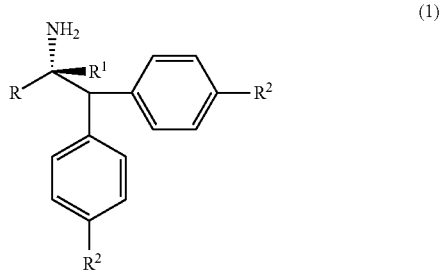

(1)

wherein, R, R$^1$ and R$^2$ is independently selected from H, C$_1$-C$_{10}$ linear or branched or cyclic alkyl, substituted or unsubstituted Aryl, ester, hetero aryl, halo, haloalkyl.

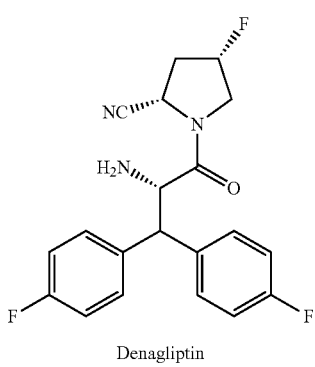

Denagliptin

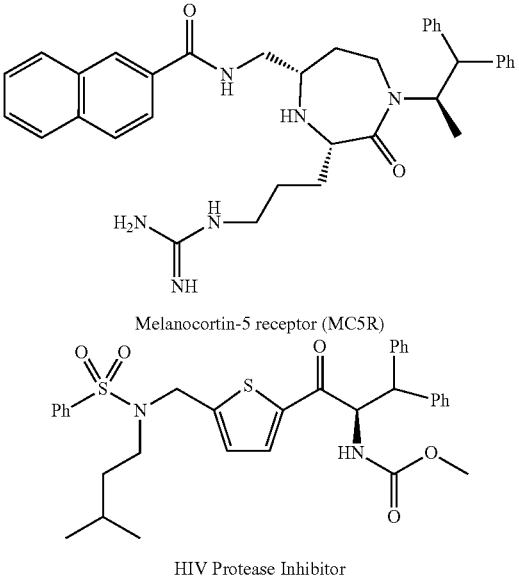

Melanocortin-5 receptor (MC5R)

HIV Protease Inhibitor

The amine compounds of formula (1) being an important intermediate for several bioactive compounds; a number of processes for its preparation are known in the art.

The journal article *Tetrahedron: Asymmetry* 10, p 1189-1192 (1999) disclosed the synthesis of (S)-alpha-(diphenylmethyl) alkyl amines from amino acids. For instance, the article disclosed a general transformation wherein the amino alcohols were treated with diphosgene to generate the oxazolidinones and the hydrogenation of the oxazolidinones proved straightforward and the target amines were readily purified.

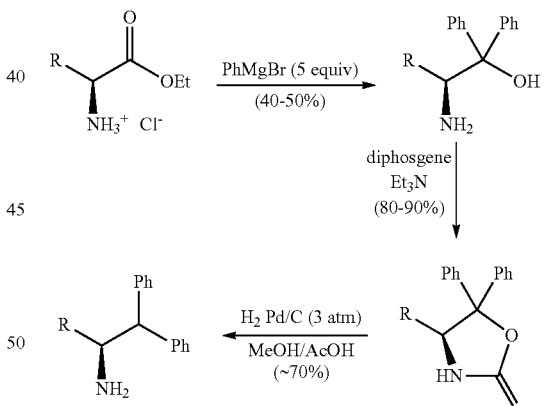

The journal articles *Tetrahedron: Asymmetry*, Vol. 8, No. 1, pp. 149-153 (1997) and Tetrahedron: Asymmetry 10, p 1189-1192 (1999) disclosed the synthesis of (S)-2-(diphenylmethyl)pyrrolidine from corresponding proline. For instance, the article disclosed a transformation wherein the (S)-L-proline was treated with ethyl chloroformate and potassium carbonate in methanol furnished corresponding ester. The product was subjected directly to a Grignard reaction with phenylmagnesium bromide (2 equivalents), which on in situ cyclisation generated cyclic compound; this compound on subsequent hydrogenation using palladium on carbon as a catalyst provided the (S)-2-(diphenylmethyl) pyrrolidine.

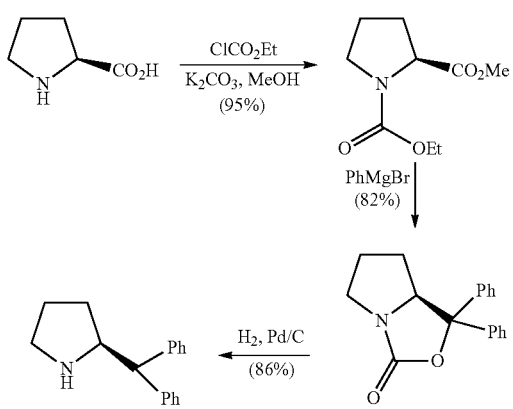 [SMILES: O=C(O)[C@@H]1CCCN1 ; CCOC(=O)N1CCC[C@H]1C(=O)OC ; c1ccc(C(c2ccccc2)[C@@H]2CCCN2)cc1 ; O=C1OC(c2ccccc2)(c2ccccc2)[C@@H]2CCCN12 ; "ClCO2Et"]

The journal article Organic Process Research & Development 17(1), 69-76 (2013) disclosed the synthesis of (S)—N-Boc bis(4-fluorophenyl)alanine from corresponding diarylketone. For instance, the article disclosed a transformation wherein the ethyl isocyanoacetate was reacted with 4,4'-difluorobenzophenone in the presence of base afforded the required N-formyl dehydroamino ester. The compound was further converted to ethyl 2-acetamido-3,3-bis(4-fluorophenyl)acrylate and ethyl 2-((tert-butoxycarbonyl)amino)-3,3-bis(4-fluorophenyl)acrylate separately by forming the diamide with the appropriate anhydride followed by treatment with methanolic potassium carbonate.

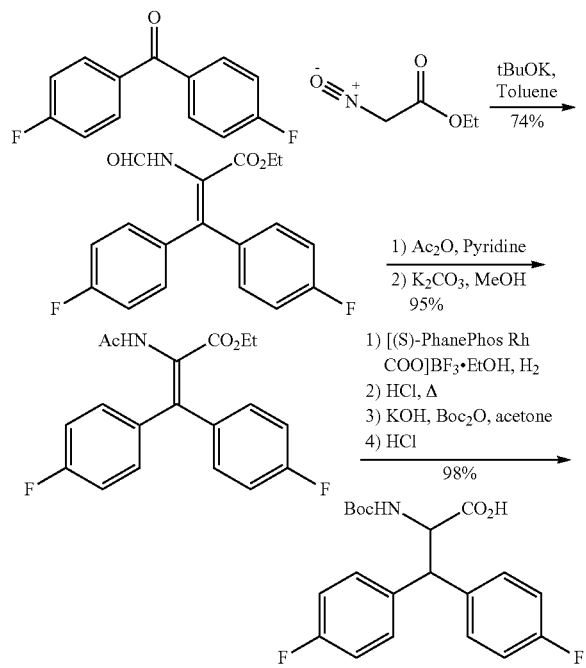

It is evident from the above cited references that the processes for the preparation of the alpha-(diarylmethyl) alkyl amines (1), described in the afore cited patent documents that the reported methods primarily involve critical reaction conditions, reagents and lengthy workup procedures. For instance, the prior art procedure involves use of multiple process steps to arrive at final amine compound which involves Grignard reaction, cyclisation and metal catalysted hydrogenation. In general, the Grignard reactions are moisture sensitive hence my lead to generate multiple impurities hence is critical to handle at industrial level. Also, the reported processes involve complex reagents and lengthy workup procedures, which renders the process costlier and hence the process is not industrially feasible.

In view of these drawbacks, there is a need to develop an industrially viable commercial process for the preparation of the compounds of formula (1); which is simple, efficient and cost-effective process and provides the desired compounds in improved yield and purity.

Inventors of the present invention have developed an improved process that addresses the problems associated with the processes reported in the prior art. The inventors of the instant invention reasoned that a direct method to access enantio-enriched alpha-(diarylmethyl) alkyl amines (1) would be an asymmetric addition of diarylmethyl anion to Ellman's Imines, which has not been explicitly reported in the art on the currently considered chemical moieties. These reaction conditions, however, surprisingly led to an unusual substrate specific regioselection lithiation of alpha-diarylmethanes. The inventors envisages that these synthetic effort could be of value in a variety of research applications, including the discovery of the known as well as new bioactive substances, and also can be extended to broad substrate scope. The process of the present invention does not involve use of any toxic, critical and/or costly catalysts, solvents and reagents. Moreover, the process does not require additional purification and critical crystallization procedure. Accordingly, the present invention provides a process for the preparation of the alpha-(diarylmethyl) alkyl amines (1) its intermediates; which is simple, efficient, cost effective, environmentally friendly and commercially scalable for large scale operations.

SUMMARY OF THE INVENTION

In one aspect, the present invention relates to an improved process for the preparation of alpha-(diarylmethyl) alkyl amine (1) comprising, reacting lithiated diarylmethyl (3-Li) anion with N-tert-butanesulfinylimine (2) to produce alpha-(diarylmethyl) alkyl amine (4); and subsequently removing the sulfinyl group.

In one aspect, the present invention relates to an improved process for the preparation of alpha-(diarylmethyl) alkyl amine (4) comprising, reacting lithiated diarylmethyl (3-Li) anion with N-tert-butanesulfinylimine (2).

In one aspect, the present invention relates to an improved process for the preparation of alpha-(diarylmethyl) alkyl amine (1) comprising, (a) reacting diarylmethyl compound (3) with N-tert-butanesulfinylimine (2) in the presence of lithiating agent;

(b) removing the sulfinyl group from the compound alpha-(diarylmethyl) alkyl amine (4) of stage (a).

In another aspect, the present invention relates to an improved process for the preparation of chiral amine (1") comprising, reacting o-lithiated diarylmethyl compound (6-Li) anion with N-tert-butanesulfinylimine (2) to produce sulfinyl amine (5); and subsequently removing the sulfinyl group.

In one aspect, the present invention relates to an improved process for the preparation of sulfinyl amine (5) comprising, reacting o-lithiated diarylmethyl compound (6-Li) anion with N-tert-butanesulfinylimine (2).

In one aspect, the present invention relates to an improved process for the preparation of chiral amine (1") comprising, (x) reacting diarylmethyl (6) with N-tert-butanesulfinylimine (2) in the presence of lithiating agent;

(y) removing the sulfinyl group from the compound sulfinyl amine (5) of stage (x).

DETAILED DESCRIPTION OF THE INVENTION

Accordingly, the present invention relates to an improved process for the preparation of alpha-(diarylmethyl) alkyl amine (1) represented by the following formula,

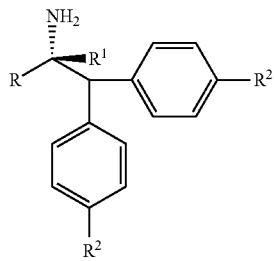

(1)

wherein, R, $R^1$ and $R^2$ is independently selected from H, $C_1$-$C_{10}$ linear or branched or cyclic alkyl, substituted or unsubstituted Aryl, ester, hetero aryl, halo, haloalkyl. comprising;

(a) reacting diarylmethyl compound (3) represented by the following formula,

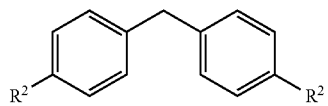

(3)

with N-tert-butanesulfinylimine compound (2) represented by the following formula,

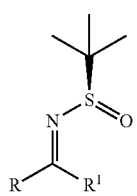

(2)

in the presence of a lithiating agent;

(b) removing the sulfinyl group from the compound alpha-(diarylmethyl) alkyl amine compound (4) of stage (a) represented by the following formula,

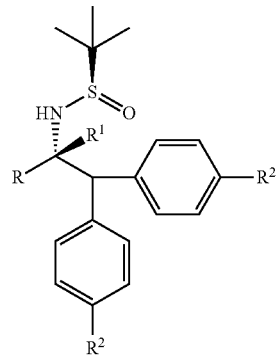

(4)

The compound (1) obtained by the afore described process is optionally converted into various therapeutically active drugs or advanced drug intermediates.

In an embodiment, the lithiating agent used at step (a) is an organolithium compound selected from n-butyl lithium (n-BuLi), phenyllithium, methyllithium, tert-butyllithium or mixture thereof.

In an embodiment, the lithiating agent used is n-Butyl Lithium (n-BuLi).

Accordingly, the present invention relates to an improved process for the preparation of alpha-(diarylmethyl) alkyl amine compound (4) represented by the following formula, (4)

wherein, R, $R^1$ and $R^2$ is independently selected from H, $C_1$-$C_{10}$ linear or branched or cyclic alkyl, substituted or unsubstituted Aryl, ester, hetero aryl, halo, haloalkyl; comprising, reacting lithiated diarylmethyl anion of compound (3-Li) represented by the following formula,

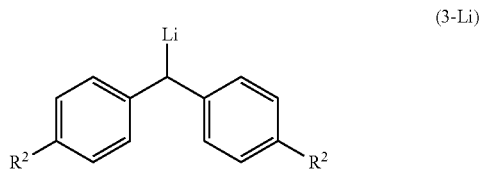

(3-Li)

with N-tert-butanesulfinylimine compound (2) represented by the following formula,

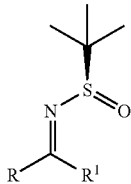

(2)

The compound (4) obtained by the afore described process is optionally converted into alpha-(diarylmethyl) alkyl amine (1) by removing the sulfinyl group from the compound alpha-(diarylmethyl) alkyl amine (4).

In the context of the present invention, the term "optionally" when used in reference to any element; including a process step e.g. optionally converted; it is intended to mean that the subject compound is subsequently converted, or alternatively, is not converted into the compound (1). Both alternatives are intended to be within the scope of the present invention.

In a specific embodiment, the process for the preparation of alpha-(diarylmethyl) alkyl amine (1) comprises the steps of;

(i) dissolving diarylmethyl compound (3) in a solvent;

(ii) cooling the reaction mixture of stage (i) to a temperature of about 0° C.;

(iii) adding n-Butyl Lithium (n-BuLi) to the stirring solution of stage (ii);

(iv) cooling the reaction mixture of stage (iii) to a temperature of about −78° C.;

(v) adding N-tert-butanesulfinylimine (2) to the stirring solution of stage (iv);

(vi) stirring the reaction mixture of stage (v) at a temperature of about −78° C.;

(vii) isolating the alpha-(diarylmethyl) alkyl amine compound (4);

(viii) removing the sulfinyl group.

The process of the present invention as per the specific embodiment described above is illustrated in the following Scheme (A);

Scheme-(A)

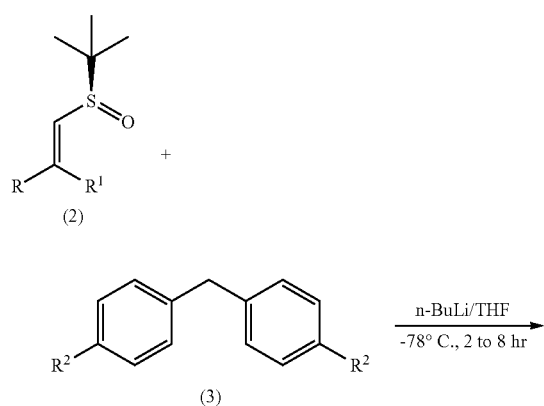

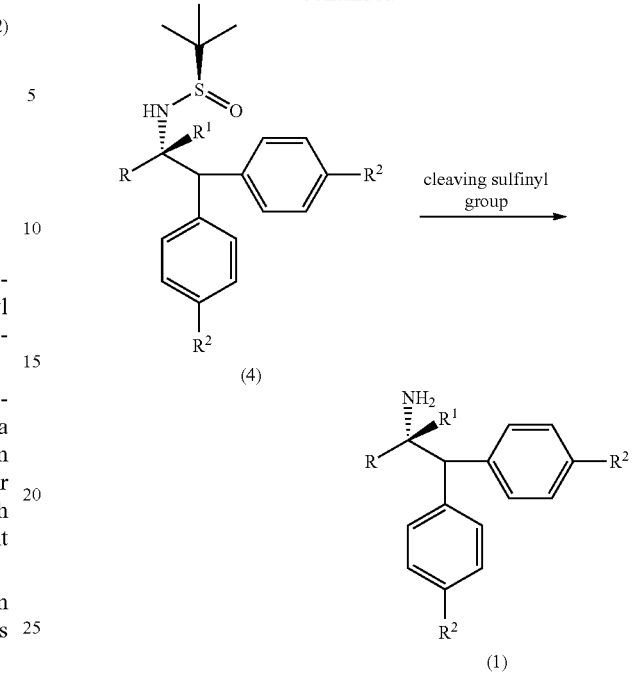

wherein, R, $R^1$ and $R^2$ is independently selected from H, $C_1$-$C_{10}$ linear or branched or cyclic alkyl, substituted or unsubstituted Aryl, ester, hetero aryl, halo, haloalkyl.

The solvent used in any of the process steps from the step (i) to step (viii) of the above process (as depicted in the Scheme (A)) is selected from an ether solvent such as tetrahydrofuran, cyclopentyl methyl ether, 2-methyltetrahydrofuran, diethyl ether, dioxane, 1,4-dioxane, 1,2-dioxane and 1,3-dioxane; an alcoholic solvent such as methanol, ethanol, isopropanol, t-amyl alcohol, t-butyl alcohol and hexanol; halogenated solvent such as dichloromethane, 4-bromotoluene, diiodomethane, carbon tetrachloride, chlorobenzene and chloroform; ketone such as acetone; an aprotic solvent such as acetonitrile, N,N-dimethyl formamide (DMF), N,N-dimethyl acetamide, dimethyl sulfoxide (DMSO) and N-methylpyrrolidone (NMP); an aromatic solvent such as toluene, xylene and benzene; water or a mixture thereof.

The term 'temperature of about 0° C.' referred to in the step (ii) of the above process (as depicted in the Scheme (A)) can range from −5° C. to +5° C.

The term 'temperature of about −78° C.' referred to in the step (iv) or (vi) of the above process (as depicted in the Scheme (A)) can range from −70° C. to −90° C.

The term 'isolating' the compound referred to in any process step from step (i) to step (viii) corresponds to the isolating or separating the obtained product using methods that corresponds to the steps involving addition of water, biphasic solvent workup, separation of solvent layers or precipitation, evaporation of solvent, filtration, washing and drying.

The term 'removing the sulfinyl group' the compound referred to in any process step (viii) corresponds to the cleaving of the sulfinyl substitution of the amine and producing the free amine compound. The removal of the sulfinyl group is achieved by treatment of the compound (4) with an acid, for example hydrochloric acid, hydrobromic acid, hydrofluoric acid, nitric acid, sulfuric acid, phosphoric acid or mixture thereof.

The inventors of the instant invention reasoned that a direct method to access enantio-enriched alpha-(diarylmethyl) alkyl amines would be an asymmetric addition of diarylmethyl anion to Ellman's Imines, which has not been explicitly reported in the art on the currently considered chemical moieties. These reaction conditions, however, surprisingly led to an unusual substrate specific regioselection lithiation of alpha-diarylmethanes. The inventors envisages that these synthetic effort could be of value in a variety of research applications, including the discovery of the known as well as new bioactive substances; such as Denagliptin, Melanocortin-5 receptor (MC5R) active substance, HIV Protease Inhibitor active compounds and so on.

The process of the present invention as per the specific embodiment described above is illustrated in the following Scheme (B);

Scheme (B)

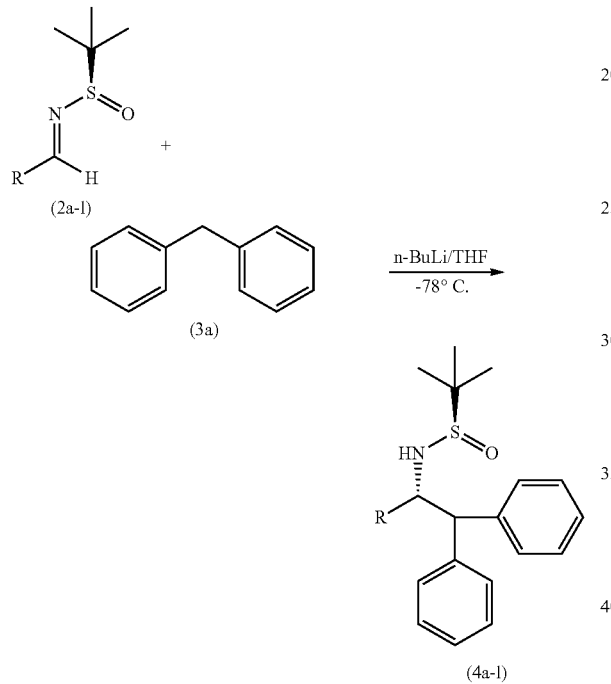

(2a-l)

(3a)

n-BuLi/THF
-78° C.

(4a-l)

wherein R represents variable as listed in below Table-1.

In the representative case illustrated below wherein the addition of diarylmethyl (3a) nucleophile to various N-tert-Butanesulfinyl aldimines (2a-l) was studied. For instance, the reaction of 2a with diphenylmethyl lithium (3a-Li) in THF at −78° C. for 2 h afforded alpha-(dipheylmethyl) phenyl amine derivative 4a in about 93% yield and with a high diastereomeric ratio (dr 98:2). The diastereoselectivity of the reaction was determined to be 98:2 by $^1$H NMR analysis of the crude product. The obtained compound (4a-l) was further treated with hydrochloric acid to remove the sulfinyl group.

TABLE 1

Addition of diarylmethyl nucleophile to various N-tert-Butanesulfinyl Aldimines[a]

| Substrate (R) | product | yield (%)[b] | dr[c] |
|---|---|---|---|
| 2a: R = Ph | 4a | 93 | >98:2 |
| 2b: R = o-ClC$_6$H$_5$ | 4b | 90 | >98:2 |
| 2c: R = p-Cl-o-FC$_6$H$_4$ | 4c | 91 | >98:2 |
| 2d: R = p-MeC$_6$H$_5$ | 4d | 90 | >98:2 |

TABLE 1-continued

Addition of diarylmethyl nucleophile to various N-tert-Butanesulfinyl Aldimines[a]

| Substrate (R) | product | yield (%)[b] | dr[c] |
|---|---|---|---|
| 2e: R = p-MeoC$_6$H$_5$ | 4e | 95 | >98:2 |
| 2f: R = 2-Furyl | 4f | 91 | >98:2 |
| 2g: R = 2-Thiophenyl | 4g | 92 | >98:2 |
| 2h: R = Cinnamyl | 4h | 92 | >98:2 |
| 2i: R = 3-ph-propionyl | 4i | 90 | >98:2 |
| 2j: R = Isopropyl | 4j | 93 | >98:2 |
| 2k: R = Isovaleryl | 4k | 94 | >98:2 |
| 2l: R = n-Butyl | 4l | 90 | >98:2 |

[a]All the reactions performed with 1.0 equiv of 2 and 2.0 equiv of 3a at −78° C. for 2 h, unless stated otherwise indicate; [b]Isolated yield; [c]The diastereoselectivity was determined by $^1$H NMR analysis. The ">98:2" dr denotes that signal for only one diastereomer were observed In another embodiment, there is provided an improved process for the preparation of chiral amine (1″) comprising, reacting o-lithiated diarylmethyl compound (6-Li) anion with N-tert-butanesulfinylimine (2) to produce sulfinyl amine (5); and subsequently removing the sulfinyl group.

In a further embodiment, there is provided an improved process for the preparation of sulfinyl amine (5) comprising, reacting o-lithiated diarylmethyl compound (6-Li) anion with N-tert-butanesulfinylimine (2).

Accordingly, the present invention relates to an improved process for the preparation of a chiral amine compound (1″) represented by the following formula,

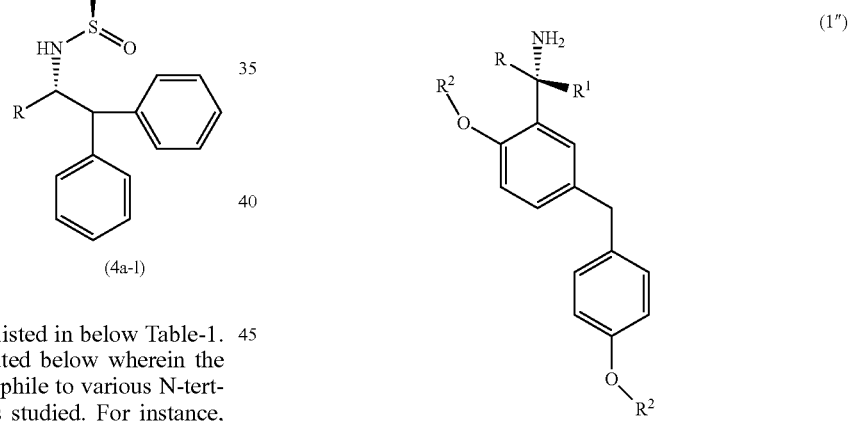

(1″)

wherein, R, R$^1$, R$^2$ is independently selected from H, C$_1$-C$_{10}$ linear or branched alkyl, substituted or unsubstituted Aryl, ester, hetero aryl, halo, haloalkyl. comprising;

(x) reacting diarylmethyl compound (6) represented by the following formula,

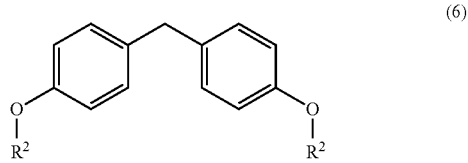

(6)

with N-tert-butanesulfinylimine compound (2) represented by the following formula,

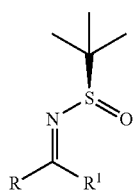

in the presence of a lithiating agent;

(y) removing the sulfinyl group from the compound sulfinyl amine (5) of stage (x) represented by the following formula,

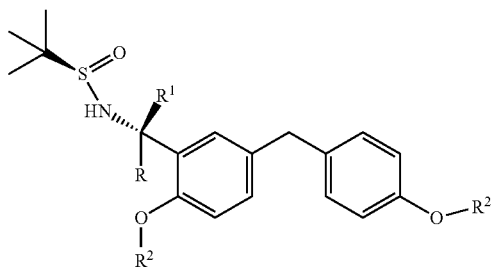

The compound (1") obtained by the afore described process is optionally converted into various therapeutically active drugs or advanced drug intermediates.

In an embodiment, the lithiating agent used at step (x) is an organolithium compound selected from n-butyl lithium (n-BuLi), phenyllithium, methyllithium, tert-butyllithium or mixture thereof.

In an embodiment, the lithiating agent used is n-Butyl Lithium (n-BuLi).

Accordingly, the present invention relates to an improved process for the preparation of sulfinyl amine compound (5) represented by the following formula,

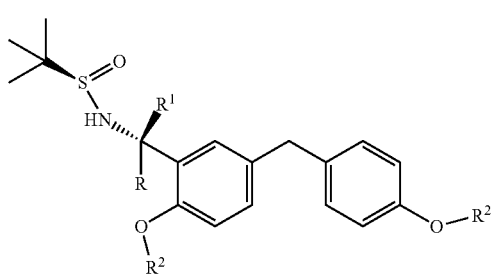

wherein, R, R$^1$ and R$^2$ is independently selected from H, C$_1$-C$_{10}$ linear or branched alkyl, substituted or unsubstituted Aryl, ester, hetero aryl, halo, haloalkyl. comprising, reacting o-lithiated diarylmethyl anion of compound (6-Li) represented by the following formula,

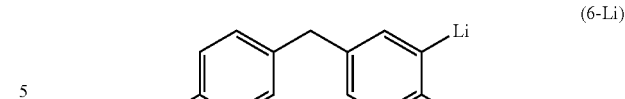

with N-tert-butanesulfinylimine compound (2) represented by the following formula,

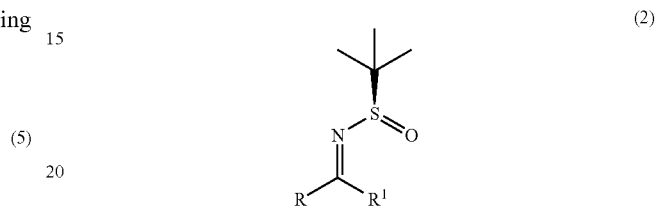

The compound (5) obtained by the afore described process is optionally converted into chiral amine (1") by removing the sulfinyl group from the compound sulfinyl amine (5).

In the context of the present invention, the term "optionally" when used in reference to any element; including a process step e.g. optionally converted; it is intended to mean that the subject compound is subsequently converted, or alternatively, is not converted into the compound (1"). Both alternatives are intended to be within the scope of the present invention.

In a specific embodiment, the process for the preparation of a chiral amine compound (1") comprises the steps of;

(xi) dissolving diarylmethyl compound (6) in a solvent;

(xii) cooling the reaction mixture of stage (xi) to a temperature of about 0° C.;

(xiii) adding n-Butyl Lithium (n-BuLi) to the stirring solution of stage (xii);

(xiv) cooling the reaction mixture of stage (xiii) to a temperature of about −78° C.;

(xv) adding N-tert-butanesulfinylimine (2) to the stirring solution of stage (xiv);

(xvi) stirring the reaction mixture of stage (xv) at a temperature of about −78° C.;

(xvii) isolating the sulfinyl amine compound (5);

(xviii) removing the sulfinyl group.

The process of the present invention as per the specific embodiment described above is illustrated in the following Scheme (C);

Scheme-(C)

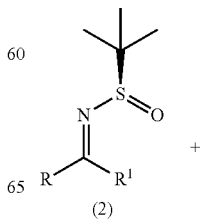

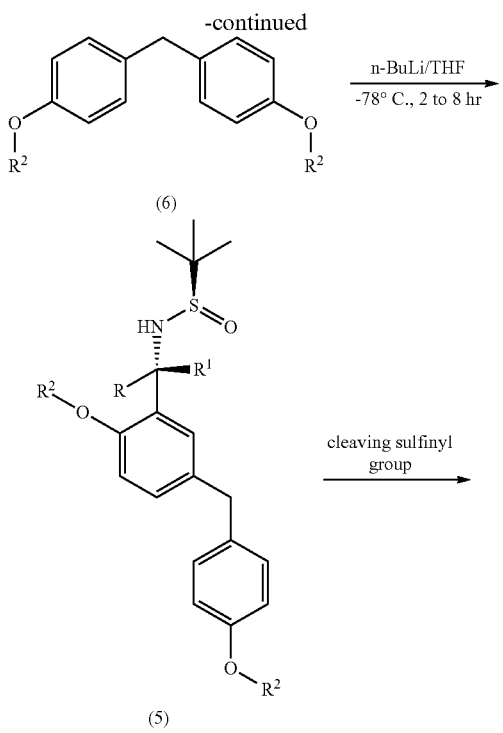

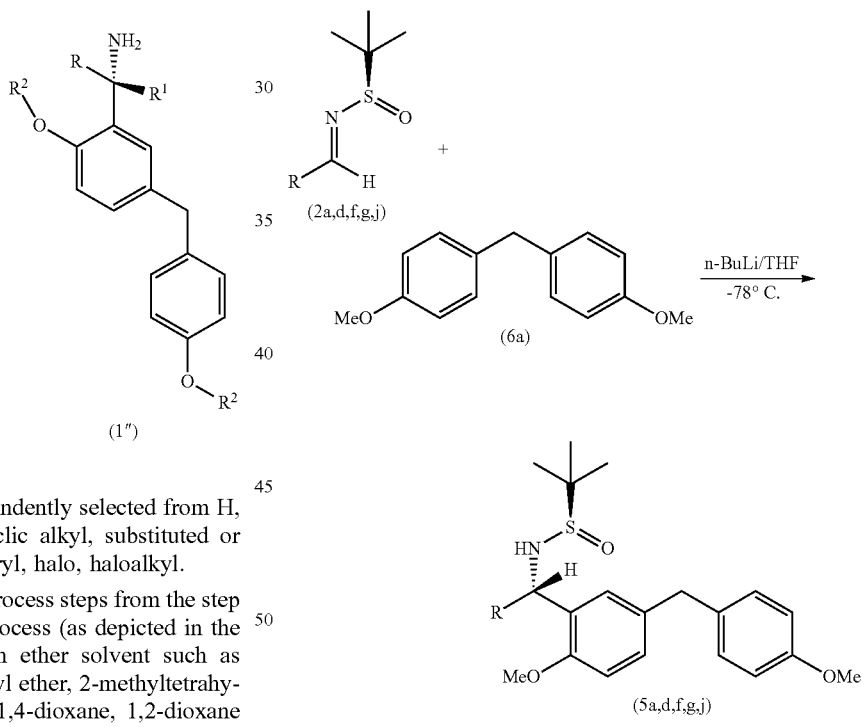

wherein, R, $R^1$ and $R^2$ is independently selected from H, $C_1$-$C_{10}$ linear or branched or cyclic alkyl, substituted or unsubstituted Aryl, ester, hetero aryl, halo, haloalkyl.

The solvent used in any of the process steps from the step (xi) to step (xviii) of the above process (as depicted in the Scheme (C)) is selected from an ether solvent such as tetrahydrofuran, cyclopentyl methyl ether, 2-methyltetrahydrofuran, diethyl ether, dioxane, 1,4-dioxane, 1,2-dioxane and 1,3-dioxane; an alcoholic solvent such as methanol, ethanol, isopropanol, t-amyl alcohol, t-butyl alcohol and hexanol; halogenated solvent such as dichloromethane, 4-bromotoluene, diiodomethane, carbon tetrachloride, chlorobenzene and chloroform; ketone such as acetone; an aprotic solvent such as acetonitrile, N,N-dimethyl formamide (DMF), N,N-dimethyl acetamide, dimethyl sulfoxide (DMSO) and N-methylpyrrolidone (NMP); an aromatic solvent such as toluene, xylene and benzene; water or a mixture thereof.

The term 'temperature of about 0° C.' referred to in the step (xii) of the above process (as depicted in the Scheme (C)) can range from −5° C. to +5° C.

The term 'temperature of about −78° C.' referred to in the step (xiv) or (xvi) of the above process (as depicted in the Scheme (C)) can range from −70° C. to −90° C.

The term 'isolating' the compound referred to in any process step from step (xi) to step (xviii) corresponds to the isolating or separating the obtained product using methods that corresponds to the steps involving addition of water, biphasic solvent workup, separation of solvent layers or precipitation, evaporation of solvent, filtration, washing and drying.

The term 'removing the sulfinyl group' the compound referred to in any process step (xviii) corresponds to the cleaving of the sulfinyl substitution of the amine and producing the free amine compound. The removal of the sulfinyl group is achieved by treatment of the compound (5) with an acid, for example hydrochloric acid, hydrobromic acid, hydrofluoric acid, nitric acid, sulfuric acid, phosphoric acid or mixture thereof.

The process of the present invention as per the specific embodiment described above is illustrated in the following Scheme (D);

wherein R represents variable as listed in below Table-2.

In the representative case illustrated below wherein the addition of diarylmethyl (6a) nucleophile to various N-tert-Butanesulfinyl aldimines (2a,d,f,g,j) was studied. For instance, the reaction of 2a with diphenylmethyl o-lithium (6a-Li) in THF at −78° C. for 2 h afforded sulfinyl amine derivative (5a) in about 90-95% yield and with a high diastereomeric ratio (dr 90:10 to 95:5) by $^1$H NMR analysis of the crude product. The obtained compound (5a,d,f,g,j) was further treated with hydrochloric acid to remove the sulfinyl group.

TABLE 2

Addition of o-lithiated diarylmethyl nucleophile to various N-tert-Butanesulfinyl Aldimines[a]

| Substrate (R) | product | yield (%)[b] | dr[c] |
|---|---|---|---|
| 2a: R = Ph | 5a | 92 | >94:6 |
| 2d: R = p-MeC$_6$H$_5$ | 5d | 90 | >95:5 |
| 2f: R = 2-Furyl | 4f | 92 | >92:8 |
| 2g: R = 2-Thiophenyl | 5g | 94 | >90:10 |
| 2j: R = Isopropyl | 5j | 95 | >95:5 |

[a]All the reactions performed with 1.0 equiv of 2 and 2.0 equiv of 6a at −78° C. for 2 h, unless stated otherwise indicate; [b]Isolated yield; [c]The diastereoselectivity was determined by $^1$H NMR analysis.

It is evident that, the instantly presented invention is an unusual substrate specific regioselective lithiation of alpha-Diarylmethanes and followed by highly diastereoselective addition to N-tert-butanesulfinylimines resulting in the selective formation of chiral alpha-(diarylmethyl) alkyl amines (4) and chiral amine (5). Advantageously, the above identified elements of the process of the instant invention effectively contribute to the reduction of overall cost of the process.

The invention is further illustrated by the following examples which are provided to be exemplary of the invention, and do not limit the scope of the invention. While the present invention has been described in terms of its specific embodiments, certain modifications and equivalents will be apparent to those skilled in the art and are intended to be included within the scope of the present invention.

EXAMPLES

Example-1: (R)-2-methyl-N-((R)-1,2,2-triphenylethyl)propane-2-sulfinamide (4a)

Charged 2.5 mL of tetrahydrofuran (THF) in a flask followed by the addition of biphenyl methane (3) (4.77 mmol) and n-butyl lithium (1.6 M in cyclohexane, 2.86 mmol) at a temperature of about 0° C. The reaction mixture was further cooled down to a temperature of about −78° C. and to the stirring solution was added N-tert-butanesulfinyl aldimine (2a) (200 mg, 0.95 mmol). The reaction mixture was continued for stirring for about 1 hr at −78° C. temperature; followed by the dropwise addition of water (5 mL) at same temperature. The reaction mixture was extracted with ethyl acetate (5 mL×3) and the separated organic layer was evaporated to provide compound (4a) with yield (330 mg, 93%).

Example-2: (R)-N-((R)-1-(2-chlorophenyl)-2,2-diphenylethyl)-2-methylpropane-2-sulfinamide (4b)

Charged 2.5 mL of tetrahydrofuran (THF) in a flask followed by the addition of biphenyl methane (3) (4.1 mmol) and n-butyl lithium (1.6 M in cyclohexane, 2.46 mmol) at a temperature of about 0° C. The reaction mixture was further cooled down to a temperature of about −78° C. and to the stirring solution was added N-tert-butanesulfinyl aldimine (2b) (200 mg, 0.82 mmol). The reaction mixture was continued for stirring for about 1 hr at −78° C. temperature; followed by the dropwise addition of water (5 mL) at same temperature. The reaction mixture was extracted with ethyl acetate (5 mL×3) and the separated organic layer was evaporated to provide compound (4b) with yield (300 mg, 90%).

Example-3: (R)-N-((R)-1-(2-chloro-4-fluorophenyl)-2,2-diphenylethyl)-2-methylpropane-2-sulfinamide (4c)

Charged 2.5 mL of tetrahydrofuran (THF) in a flask followed by the addition of biphenyl methane (3) (3.82 mmol) and n-butyl lithium (1.6 M in cyclohexane, 2.29 mmol) at a temperature of about 0° C. The reaction mixture was further cooled down to a temperature of about −78° C. and to the stirring solution was added N-tert-butanesulfinyl aldimine (2c) (200 mg, 0.76 mmol). The reaction mixture was continued for stirring for about 1 hr at −78° C. temperature; followed by the dropwise addition of water (5 mL) at same temperature. The reaction mixture was extracted with ethyl acetate (5 mL×3) and the separated organic layer was evaporated to provide compound (4c) with yield (290 mg, 91%).

Example-4: (R)-2-methyl-N-((S)-3-methyl-1,1-diphenylbutan-2-yl)propane-2-sulfinamide (4j)

Charged 2.5 mL of tetrahydrofuran (THF) in a flask followed by the addition of biphenyl methane (3) (8.55 mmol) and n-butyl lithium (1.6 M in cyclohexane, 5.13 mmol) at a temperature of about 0° C. The reaction mixture was further cooled down to a temperature of about −78° C. and to the stirring solution was added N-tert-butanesulfinyl aldimine (2j) (300 mg, 1.71 mmol). The reaction mixture was continued for stirring for about 1 hr at −78° C. temperature; followed by the dropwise addition of water (5 mL) at same temperature. The reaction mixture was extracted with ethyl acetate (5 mL×3) and the separated organic layer was evaporated to provide compound (4j) with yield (546 mg, 93%).

Example-5: (S)-3-methyl-1,1-diphenylbutan-2-amine (1j)

Charged 1 mL of Dioxane in a flask followed by the addition of alpha-(diarylmethyl) alkyl amine 4j (100 mg, 0.29 mmol) and hydrochloric acid solution (4.0 M in dioxane, 2.9 mmol, 0.72 mL). The reaction mixture was stirred for 2 hr at room temperature and the reaction mixture was concentrated under vacuum. To the crude residue was added water (2 mL), followed by the addition of 6 M NaOH aqueous solution to adjust the pH 12-13. The reaction mixture was extracted with ethyl acetate (5 mL×3) and the separated organic layer was evaporated to provide free amine compound (1j) yield (69 mg).

Example-6: (S)-4-methyl-1,1-diphenylpentan-2-amine (1k)

Charged 1 mL of Dioxane in a flask followed by the addition of alpha-(diarylmethyl) alkyl amine 4k (100 mg, 0.28 mmol) and hydrochloric acid solution (4.0 M in dioxane, 2.8 mmol, 0.7 mL). The reaction mixture was stirred for 2 hr at room temperature and the reaction mixture was concentrated under vacuum. To the crude residue was added water (2 mL), followed by the addition of 6 M NaOH aqueous solution to adjust the pH 12-13. The reaction mixture was extracted with ethyl acetate (5 mL×3) and the separated organic layer was evaporated to provide free amine compound (1k) yield (70 mg).

Example-7: (S)-N-((R)-(2-methoxy-5-(4-methoxy-benzyl)phenyl)(phenyl)methyl)-2-methylpropane-2-sulfinamide (5a)

Charged 2.5 mL of tetrahydrofuran (THF) in a flask followed by the addition of bis(4-methoxyphenyl)methane (6a) (4.77 mmol) and n-butyl lithium (1.6 M in cyclohexane, 2.86 mmol) at a temperature of about 0° C. The reaction mixture was further cooled down to a temperature of about −78° C. and to the stirring solution was added N-tert-butanesulfinyl aldimine (2a) (200 mg, 0.95 mmol). The reaction mixture was continued for stirring for about 1 hr at −78° C. temperature; followed by the dropwise addition of water (5 mL) at same temperature. The reaction mixture was extracted with ethyl acetate (5 mL×3) and the separated organic layer was evaporated to provide compound (5a) with yield (384 mg, 92%).

Example-8: (S)-N-((R)-(2-methoxy-5-(4-methoxy-benzyl)phenyl)(p-tolyl)methyl)-2-methylpropane-2-sulfinamide (5d)

Charged 2.5 mL of tetrahydrofuran (THF) in a flask followed by the addition of bis(4-methoxyphenyl)methane (6a) (5.59 mmol) and n-butyl lithium (1.6 M in cyclohexane, 3.35 mmol) at a temperature of about 0° C. The reaction mixture was further cooled down to a temperature of about −78° C. and to the stirring solution was added N-tert-butanesulfinyl aldimine (2d) (247 mg, 1.11 mmol). The reaction mixture was continued for stirring for about 1 hr at −78° C. temperature; followed by the dropwise addition of water (5 mL) at same temperature. The reaction mixture was extracted with ethyl acetate (5 mL×3) and the separated organic layer was evaporated to provide compound (5d) with yield (460 mg, 92%).

Example-9: (S)-N-((S)-furan-2-yl(2-methoxy-5-(4-methoxybenzyl)phenyl)methyl)-2-methylpropane-2-sulfinamide (5f)

Charged 2.5 mL of tetrahydrofuran (THF) in a flask followed by the addition of bis(4-methoxyphenyl)methane (6a) (6.27 mmol) and n-butyl lithium (1.6 M in cyclohexane, 3.76 mmol) at a temperature of about 0° C. The reaction mixture was further cooled down to a temperature of about −78° C. and to the stirring solution was added N-tert-butanesulfinyl aldimine (2f) (248 mg, 1.25 mmol). The reaction mixture was continued for stirring for about 1 hr at −78° C. temperature; followed by the dropwise addition of water (5 mL) at same temperature. The reaction mixture was extracted with ethyl acetate (5 mL×3) and the separated organic layer was evaporated to provide compound (5d) with yield (490 mg, 92%).

We claim:

1. A process for the preparation of a chiral amine compound (1″) or its salts, of the following formula,

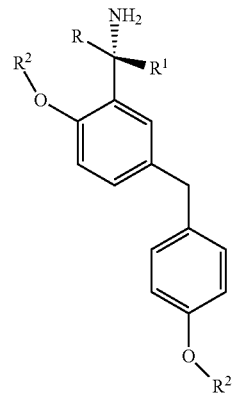

(1″)

wherein, R, $R^1$, $R^2$ is independently selected from H, $C_1$-$C_{10}$ linear or branched alkyl, substituted or unsubstituted Aryl, ester, hetero aryl, halo, haloalkyl; comprising the steps of:

(x) reacting diarylmethyl compound (6) represented by the following formula,

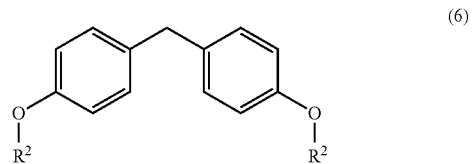

(6)

with N-tert-butanesulfinylimine compound (2) represented by the following formula,

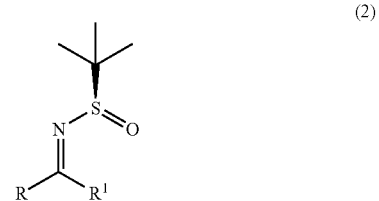

(2)

in the presence of a lithiating agent;

(y) removing the sulfinyl group from the compound sulfinyl amine (5) of stage (x) represented by the following formula,

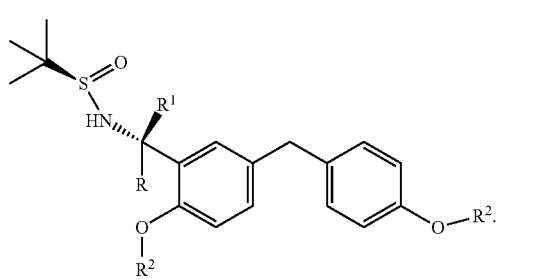

(5)

2. The process according to claim 1, wherein the step (x) involves in-situ formation of o-lithiated diarylmethyl anion compound (6-Li) of the following formula,

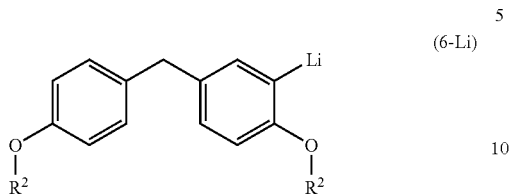

(6-Li)

wherein, $R^2$ is as defined above.

3. The process according to claim 1, wherein the lithiating agent used at step (x) is an organolithium compound selected from n-butyl lithium (n-BuLi), phenyllithium, methyllithium, tert-butyllithium or mixture thereof.

4. The process according to claim 1, wherein the step (y) involves the cleaving of the sulfinyl substitution of the amine by treatment of the sulfinyl amine compound (5) with an acid, such as hydrochloric acid, hydrobromic acid, hydrofluoric acid, nitric acid, sulfuric acid, phosphoric acid or a mixture thereof.

* * * * *